United States Patent [19]
Kroll et al.

[11] Patent Number: 5,391,186
[45] Date of Patent: Feb. 21, 1995

[54] METHOD AND APPARATUS FOR UTILIZING SHORT TAU CAPACITORS IN AN IMPLANTABLE CARDIOVERTER DEFIBRILLATOR

[75] Inventors: Mark W. Kroll; Kai C. Kroll, both of Minnetonka, Minn.

[73] Assignee: Angeion Corporation, Plymouth, Minn.

[21] Appl. No.: 166,216

[22] Filed: Dec. 13, 1993

[51] Int. Cl.$^6$ .............................................. A61N 1/36
[52] U.S. Cl. ............................................... 607/5
[58] Field of Search .................. 607/4, 5, 7, 8

[56] References Cited
U.S. PATENT DOCUMENTS 4,768,512  9/1988  Imran ........................ 607/5

*Primary Examiner*—William E. Kamm
*Assistant Examiner*—Scott M. Getzow
*Attorney, Agent, or Firm*—Patterson & Keough

[57] ABSTRACT

An implantable cardioverter defibrillator for treating cardiac dysrhythmias utilizing an interrupted discharge output provided by a switch control means to vary the duty cycle of a switch incorporated within the output circuitry of the implanted cardioverter defibrillator so as to increase the efficiency by extending the duration of the discharge for capacitor systems having time constants, tau, less than about the chronaxie value of the human heart. As a result, the implantable cardioverter defibrillator produces a more favorable rectangular-like waveform from the discharge of a significantly smaller capacitor than the capacitors used in existing implantable cardioverter defibrillators.

8 Claims, 8 Drawing Sheets

METHOD AND APPARATUS FOR UTILIZING SHORT TAU CAPACITORS IN AN IMPLANTABLE CARDIOVERTER DEFIBRILLATOR

RELATED APPLICATION

This application is related to an application filed in the United States Patent and Trademark Office concurrently with the present application and entitled IMPLANTABLE CARDIOVERTER DEFIBRILLATOR EMPLOYING POLYMER FILM CAPACITORS, Ser. No. 08/xxx,xxx, which is assigned to the assignee of the present invention, a copy of which is attached hereto and the disclosure of which is hereby incorporated by reference in the present application.

BACKGROUND

1. Field of the Invention

The present invention relates generally to implantable cardioverter defibrillator (ICD) system and, more specifically, to a method and apparatus for utilizing capacitors systems having effective capacitances of less than about 60 µF, i.e., short tau capacitors, in an ICD system.

2. BACKGROUND OF THE INVENTION

The incidence of heart disease in the United States is significant with approximately one out of every two deaths is attributable to heart disease. One of the leading complications secondary to heart disease is cardiac arrythmia resulting in sudden cardiac death. Because of the high prevalence of sudden cardiac death due to cardiac arrythmia there is a demonstrated need for an implantable cardioverter defibrillator (ICD) system. To be useful, an ICD systems must be self-contained, complete, and capable of effective repetitious function autonomous from the outside world. A direct corollary of these requirements is that the system be small enough to be implanted. The size limitations imposed by an implantable device generally have prevented the technology and techniques applicable to external defibrillator systems from being applied to ICD systems. Even with the development of novel technology and techniques for generating defibrillation pulses or countershocks in an implantable device, present day ICD systems are still sufficiently large so as to require implantation within the abdomen or abdominal wall of a patient.

A more ideal size for an ICD system would be the size that implantable cardiac pacemakers have achieved, such that the device is capable of being implanted in the subcutaneous space just inferior to either clavicle. Unfortunately, pacemakers are capable of smaller sizes quite simply because their power requirements are significantly less than the power requirements of ICD systems. While pacemakers have energy output requirements that are in the microjoule output range, ICD systems, to be effective, must be capable of delivering repeated defibrillation countershocks above at least about 15 joules for each countershock. In order to achieve such high energy outputs, existing ICD systems have utilized larger batteries, as well as large high voltage capacitors to generate the required high energy defibrillation countershock. Consequently, one of the major challenges in reducing the size of an ICD system is how to decrease the effective size limits of both the batteries and capacitors that are used by the ICD system.

Presently, there are three different types of ICD systems which have received device approval from the Federal Drug Administration, the PCD ™ device, available from Medtronic, Inc., of Minneapolis, Minn., the Cadence ® device, available from Ventritex, Inc., of Mountain View, Calif., and the Ventak-P ® device, available from Cardiac Pacemakers, Inc., of St. Paul, Minn. The primary components of all existing ICD systems include an automatic monitoring and detection mechanism, a capacitor system, a battery system and control circuitry for detecting a ventricular arrhythmia and controlling delivery of a high-voltage capacitive-discharge electrical countershock in response by charging and then discharging the capacitor system. To achieve successful defibrillation, the ICD system must deliver a high voltage electrical countershock with an initial voltage of greater than about 500 to 600 volts.

The existing ICD systems are all capable of delivering a maximum countershock of up to 700 to 750 volts having a total energy of between 31 to 44 joules. At the time an ICD system is implanted in a patient, the attending physician will empirically determine a minimum defibrillation threshold for the patient, and will program the charging voltages for the countershocks to be delivered as part of a therapy regimen within the range of maximum voltages allowed by the device. In addition, the attending physician can also typically program when the electrical countershock is to be truncated by programming either the duration of the countershock in a range from about 6 to 9 milliseconds. Alternatively, the duration can be altered by programming the initial discharge voltage of the ICD system and allowing the tilt of the ICD system to establish the point at which the countershock will be truncated. The tilt of an ICD system is defined as the percentage decline in the output voltage from the charging voltage to the voltage at the time the discharge is truncated. For existing ICD systems, the tilt is typically set at about 65%.

To understand why the battery and capacitor systems of existing ICD systems are designed as they are, it is helpful to examine the relationships and limitations of the various components of the ICD system that are used to produce an effective electrical countershock. To begin with, the capacitance of an ICD system is proportional to the applied charging voltage and the stored energy. The relationship is given by:

$$E = 0.5(C*V^2) \tag{1}$$

where E, in joules, is the amount of energy stored in the capacitor, C is capacitance and V is charging voltage. Transforming this equation yields:

$$C = 2(E/V^2) \tag{2}$$

Consequently, if the maximum stored energy and the maximum charging voltage of an ICD system are known, there will be a minimum effective capacitance of the ICD system that is necessary to achieve the chosen values for maximum stored energy and charging voltage. In existing ICD systems, which have maximum stored energy values of 35 to 40 joules and maximum charging voltages of 750 volts, the minimum effective capacitance of the ICD system is approximately 120 to 140 µF. In existing ICD systems, the maximum stored energy has been selected so as to provide a defibrillation threshold safey margin, and the maximum charging voltage is determined by the choise of a pair of electrolytic capacitors as the capacitor system. Thus, the effective capacitance of existing ICD systems is a value that cannot be arbitrarily chosen, but is instead dictated by other factors in the design of the ICD system.

In addition to affecting the maximum stored energy for an ICD system, the effective capacitance of an ICD system also impacts the duration of the coutnershocks whih are delivered by the ICD system. The rate of discharge of a capacitor system is given by:

$$\tau = R*C \qquad (3)$$

where R is the average myocardial tissue resistance and $\tau$ is a time constant tau of the ICD system. If the capacitance C is 140 $\mu$F and the resistance R across the myocardial muscle is 50 ohms, then, according to Eq. (3), $\tau$ equals 7 milliseconds.

The time constant $\tau$ describes the natural exponential decay of the capacitive discharge from an initial discharge voltage $V_i$ to a final discharge voltage $V_f$ at the truncation such that:

$$V_f = V_i * e^{-d/\tau} \qquad (4)$$

where d is the duration of the pulse in terms of the duration of a monophasic waveform or the end of the first phase of a biphasic waveform. When the duration d of the discharge output is truncated at about one $\tau$, as is the case for all existing ICD systems, the final discharge voltage $V_f$ will be about 38.8% of the initial discharge voltage $V_i$.

Because energy is a function of the square of the charging voltage, most of the stored energy is delivered to the heart by a countershock that has a duration of about one $\tau$. For the capacitance values and charging voltages of existing ICD systems, the percentage of stored energy that is actually discharged from the capacitor through the myocardium in about one $\tau$ is about 80 to 90% of the total stored energy. Assuming that the initial charging voltage $V_i$ is 750 volts and that C is 140 $\mu$F, for example, then the total stored energy as defined by Eq. (1) is 39.3 joules. In this case, if the electrical countershock is truncated at 7 milliseconds, then the final discharge voltage $V_f$ is 291 volts from Eq. (4). Using the final discharge voltage Vf in Eq. (1), it can be seen that 5.92 joules of energy will remain in the capacitor system. In this example, a total of 33.3 joules of energy will be delivered to the myocardium, about 85% of the total stored energy.

It can be seen from this example that truncating the discharge of existing ICD systems at a duration less than one time constant tau significantly decreases the proportion of stored energy which is actually delivered to the heart and would have the undesired effect of actually decreasing the effectiveness of the ICD system without providing any decrease in the overall size of the device.

In a co-pending application entitled IMPLANTABLE CARDIOVERTER DEFIBRILLATOR SYSTEM HAVING A SMALLER DISPLACEMENT VOLUME, Ser. No. 08/033,632, filed on Mar. 15, 1993, it is taught that the overall size of an ICD system can be decreased by decreasing the effective capacitance of the ICD system below about 120 $\mu$F. Because the size of a capacitor system is proportional to its capacitance value, a decrease in the capacitance value decreases the size of the capacitor system, and, hence, the overall size of the ICD system.

Even though the capacitance C is descreased, and therefor the energy E as defined by Eq. (1) is decreased, the ICD system of the co-pending application actually increases the overall effectiveness of the device due to the fact that when the capacitance C of the ICD system is less than 120 $\mu$F, it is more closely matched to the natural capacitance of the heart than the capacitances of existing ICD systems. As a result, the physiologically effective current delivered by a capacitor system having an effective capacitance of less than 120 $\mu$F is actually greater than that of existing ICD systems. In other words, an ICD system with a smaller capacitance is more effective than an ICD system with a larger capacitance. For a more detailed explanation of this phenomenon, reference is made to the co-pending application identified above.

While signficant decreases in the overall size of an ICD system can be obtained by decreasing the effective capacitance C of the ICD system, there is a point below which decreasing the effective capacitance of an ICD system begins to have a negative impact on the effectiveness of the defibrillation countershock. To understand why this happens, it is necesary to examine the average current of the delivered countershock.

Imagine delivering a 10 volt pulse through a resistance of 50 ohms for 10 seconds. Using Ohm's law:

$$I = V/R \qquad (5)$$

where I is current, V is voltage, and R is myocardial resistance, then the current is 0.2 amperes. The energy of the pulse is given by:

$$E = V*I*d \qquad (6)$$

where d is the pulse duration, which works out to be 10 volts $\times$ 0.2 amperes $\times$ 10 seconds which equals 20 joules of energy delivered.

Unfortunately, 20 joules of energy delivered in this fashion will never defibrillate the heart because the average current flowing through the myocardium is insufficient. Experiments dating back to the 1890's have demonstrated that there is a minimum threshold average current that is necessary to consistently achieve successful defibrillation countershocks. In these experiments, this minimum threshold was defined as the rheobase current for a particular cell in terms of the minimum average current needed to effect a successful defibrillation countershock if the current was applied for an infinite duration. This rheobase value was derived from strength-duration curves from experimental data and is the asymptotic value projected for the experimental data as the duration approached infinity.

From these experimental strength-duration curves, a value known as the chronaxie was also defined as that duration of time that requires a minimum average current threshold that is twice the rheobase to effect defibrillation. Numerous experimental studies on animal hearts have shown the defibrillation chronaxie range to be approximately 2 to 4 milliseconds. The rheobase has been shown to be approximately 5 amperes. There is no experimental or clinical reason to expect the human heart to have rheobase and chronaxie values outside this range.

The minimum threshold current needed to defibrillate a heart with a very wide pulse would be very near the rheobase of 5 amperes. Using Ohm's law and the accepted value of 50 ohms as the resistance between discharge electrodes, then a 5 amp current through 50 ohm will require 250 volts. A very wide defibrillation pulse duration, for example 40 milliseconds, will require at least 50 joules of energy to be effective using Eq. (6). Using a defibrillation chronaxie duration of 3 milliseconds, then the minimum threshold average current will be 10 amperes, or twice the rheobase. This will require a charge of 500 volts, but will effect defibrillation with only 15 joules total energy delivered in a duration of about 3 milliseconds.

For time periods shorter than the chronaxie, the minimum energy requirement begins to increase again, for example a 1 millisecond pulse will require a minimum of 20 joules to reach the defibrillation threshold. The usefulness of the chronaxie becomes apparent because it identifies the duration of discharge most efficient in terms of the energy required to successfully carry out a defibrillation. For safety concerns, all ICD systems should be able to deliver a defibrillation countershock that exceeds 500 volts, 10 amperes average current, and a 3 millisecond duration in order to ensure that the countershocks which are delivered will succeed in countershocking a fibrillating heart.

The average current of 10 amperes over 3 milliseconds is based on a rectangular waveshape. In external defibrillating devices, where system size is not a concern, the systems have been developed to deliver generally rectangular shaped waveform. On the other hand, research has shown that the exponential decay curves of a capacitive-discharge is also effective in consistently defibrillating the heart; however, the calculation for the average discharge current is not as straight forward as for a rectangular waveshape. An average discharge current for an exponential decay capacitive discharge can be calculated from the following equation:

$$I_{ave} = C*(V_i - V_f)/d \qquad (7)$$

where C is capacitance, $V_i$ is the initial charging voltage, $V_f$ is the final voltage at time d when the discharge is truncated.

Using Eq. (7), it is possible to determine a minimum effective capacitance that will deliver an Iave equal to 10 amperes when the duration d equals the chronaxie at 3 milliseconds, and $(V_i - V_f)$ equals 500 volts. Solving Eq. (7) under these conditions yields a minimum capacitance C equal to at least 60 $\mu$F in order to produce a defibrillation countershock that will meet the minimum average current, duration and voltage conditions established above.

The problem with solving Eq. (7) in this manner is that the term $(V_i - V_f)$ is not limited to any particular $V_i$. Due to the charging voltage restrictions for the pair of electrolytic capacitors used in existing ICD systems that limit $V_i$ to 750 volts, it is necessary to resolve Eq. (7) so that this limitation may be factored into the equation. Reworking Eq. (4), it is possible to define the term $(V_i - V_f)$ as related to the $\tau$ of the system by the equation:

$$V_i - V_f = V_i*(1 - e^{-d/\tau}) \qquad (8)$$

Substituting Eq. (8) for the term $(V_i - V_f)$ in Eq. (7) yields a solution to the minimum theoretical capacitance necessary for a pair of electrolytic capacitors charged to a maximum voltage of 750 volts in order to deliver a defibrillation countershock with Iave equal to 10 amperes when the duration d equals the chronaxie at 3 milliseconds, and $(V_i - V_f)$ equals 500 volts:

$$C = (I_{ave}*d)/(V_i*(1 - e^{-d/\tau})) \qquad (9)$$

Solving Eq. (9) for C under these conditions gives a value of 63 $\mu$F as the minimum theoretical capacitance for an ICD system that uses a pair of electrolytic capacitors. When this theoretical capacitance of 63 $\mu$F and a maximum charging voltage of 750 volts are used in Eq. (1), the maximum stored energy of such a theoretical ICD system would be about 17.7 joules, of which about 85% can be delivered in one time constant tau, or about 15 joules. This value corresponds with the results of experimental data that teach that the minimum efficient amount of energy needed for reliable defibrillation is 15 joules delivered over 3 milliseconds.

Even thought the solution to Eq. (9) suggests that a smaller effective capacitance could be used, existing ICD systems have been designed for a 100% stored energy safety factor such that they can provide for a maximum stored energy of at least about 35 joules, as opposed to the 17 joules stored for the theoretical minimum capacitance. This practice has dictated the use of two electrolytic capacitors with an effective capacitance in the range of at least about 140 $\mu$F. The doubling of the capacitance also doubles the time constant for the system, which in turn doubles the discharge duration. As a result, all of the ICD systems in use today have followed these guidelines and use a minimum duration of approximately 6 milliseconds, which is twice the expected defibrillation chronaxie value of 3 milliseconds, and provide for a maximum stored energy of at least 35 joules.

Even though it is known that smaller capacitances have smaller volumes, the minimum theoretical capacitance of about 60 $\mu$F appears to be a practical lower limit on the size and effective capacitance of a capacitor system for use in an ICD system. Below about 60 $\mu$F, the duration of the countershock discharge truncated at one time constant $\tau$ starts to fall below the defibrillation chronaxie value of 3 milliseconds. In other words, capacitors below this value have time constants which are too short for effective defibrillation.

Although existing ICD systems have proven effective in providing defibrillation therapy, the existing devices are larger than desirable. While it is possible to decrease the size of an ICD system by decreasing the effective capacitance and, hence, the size of the capacitor system, there is a minimum theoretical capacitance below which the effectiveness of the defibrillation countershock significantly decreases. Consequently, it would be desirable to provide for a method and apparatus which would allow an ICD system to utilize a smaller capacitor system that has an effective capacitance below the minimum theoretical capacitance without significantly decreasing the effectiveness of the defibrillation countershock generated by such a smaller capacitor system.

SUMMARY OF THE INVENTION

The present invention discloses a method and apparatus directed at conserving capacitor storage and energy requirements so as to allow for capacitors having smaller capacitance values to be utilized in an ICD system. The present invention extends the discharge duration of the capacitive-discharge of a smaller capacitor by intermittently interrupting the countershock discharge to the cardiac electrodes in such a fashion as to maintain an effective discharge across the myocardium. In extending the discharge duration of these smaller capacitors, the present invention draws not only upon the electrical and physical characteristics of the capacitors in its approach and design, but also utilizes to its advantage the inherent transmembrane capacitance of the myocardium and the electrode capacitance as well.

For purposes of the present invention, a capacitor system for an ICD system will be referred to as a short tau capacitor if the capacitor system has a characteristic time constant defined by the average myocardial resistance value multiplied by the effective capacitance value of the capacitor system that is substantially at or below the defibrillation chronaxie duration for the human patient heart. For the generally accepted values of both the average myocardial resistance and the defibrillation chronaxie duration for the human patient heart, a short tau capacitor includes any capacitor system having an effective capacitance of less than about 60 $\mu F$.

By utilizing the disclosed methods and apparatus for extending the discharge duration of a short tau capacitor, an ICD system is able to make use of significantly smaller high voltage, low capacitance components, thereby reducing the overall size of the ICD system without compromising the defibrillation effectiveness of the system. By effectively extending the duration of short tan capacitors, the present invention removes many of the limitations which have prevented the use of otherwise more efficient, higher voltage capacitor systems.

The advantages of utilizing higher voltage capacitor systems are evident when the relationships of Eq. (1) are examined. In accordance with Eq. (1), the stored energy of an ICD system is a function of the square of the charging voltage, as opposed to being only proportional to the capacitance value. Consequently, a more compact and efficient ICD system can be constructed by utilizing a higher voltage, lower capacitance capacitor system, provided that this type of capacitor system can deliver a countershock having a duration that provides for effective defibrillation. The present invention extends the duration of short tau capacitors beyond the defibrillation chronaxie duration for the human patient heart, thereby insuring that a countershock delivered from such a capacitor system will provide for effective defibrillation of the human patient heart.

The effective duration period of a short tan capacitor is lengthened in accordance with the present invention by periodic and rapid interruption of the discharge current across the cardiac electrodes. In one embodiment, the present invention comprising a power source, a short tau capacitor, a resistive divider comprised of a first resistor and a second resistor connected in parallel with the short tau capacitor, a discharge control for controlling the polarity of the discharge pulse to the cardiac electrodes, and a switch control electrically connected between the first and second resistors and to the gate of a power FET switch with source and drain connected in series between the discharge control and the short tau capacitor. The switch control intermittently interrupts the discharge of the short tau capacitor across the cardiac electrodes so as to effectively extend the discharge duration beyond the defibrillation chronaxie value of the human heart. In a preferred embodiment, the switch control means is operated asynchronously in response to an estimated voltage as seen by the cardiac electrodes.

DETAILED DESCRIPTION OF THE DRAWINGS

DETAILED DESCRIPTION OF THE PREFERRED EMBODIMENT

Figure 1:
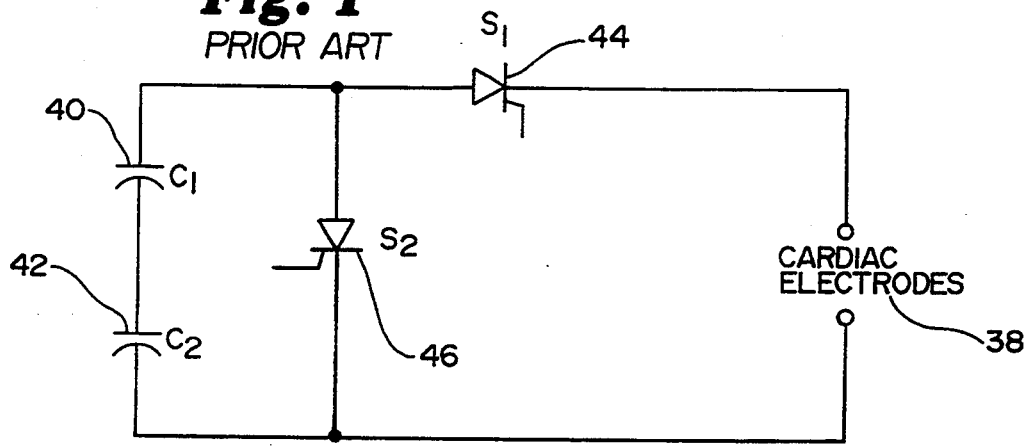
FIG. 1 is a simplified electrical schematic diagram of the original Schuder circuit for an existing ICD system.

FIG. 1 depicts a simplified diagrammatic representation of the discharge circuit for an existing implantable cardioverter defibrillator (ICD) system. High voltage capacitors 40 and 42 represent the dual electrolytic high voltage capacitors whereby capacitors 40 and 42 are each charged to approximately 375 volts by a split winding transformer 36 powered by battery source 34. Once fully charged, capacitors 40 and 42 are discharged in series through silicon controlled rectifier (SCR) 44 as the activating switch delivering the countershock to the myocardium via countershock electrodes 38. In the original Schuder circuit the countershock discharge was truncated through activation of a second SCR 46 which starves SCR 44 by shorting capacitors 40 and 42. Control circuitry 32 responds to a sensing signal (not shown) to detect the presence of a cardiac arrhythmia, and, in response, selectively controls the charging and discharging of capacitors 40 and 42. The circuit depicted in FIG. 1 is inefficient by wasting the leftover energy when terminating the defibrillation countershock in this fashion.

Figure 2:
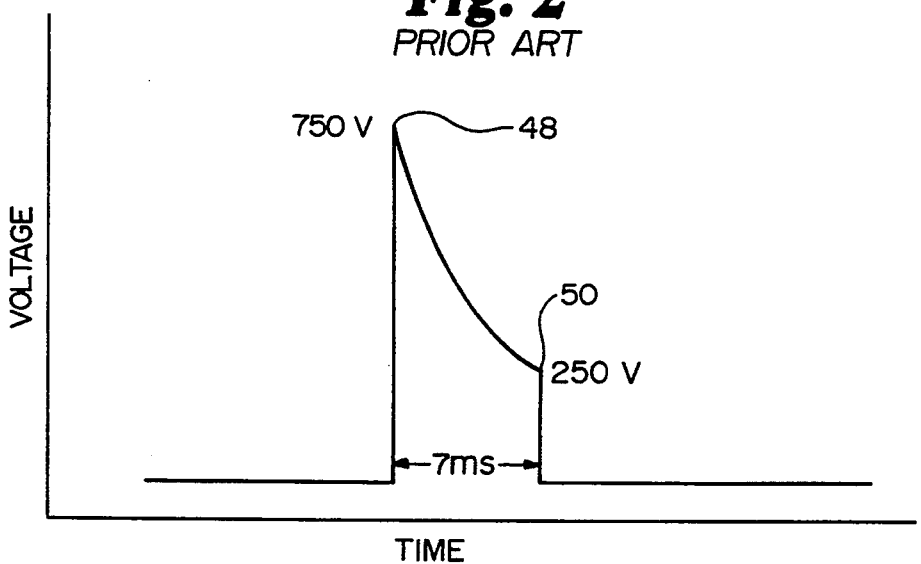
FIG. 2 is a graph depicting the voltage discharge for a typical monophasic discharge pulse generated by the circuit shown in FIG. 1.
Figure 3:
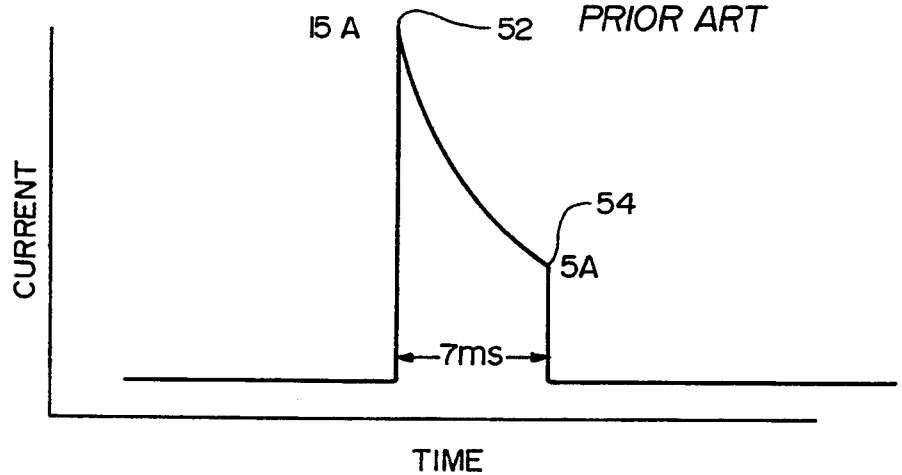
FIG. 3 is a graph depicting the current output of a monophasic pulse as shown in FIG. 2.

FIG. 2 shows a graphic representation of the voltage versus time plot of a single monophasic discharge of the Schuder circuit of FIG. 1. As shown at time point 48 there is an initial peak voltage of 750 volts to capacitors 40 and 42 that exponentially decays according to the time constant for capacitors 40 and 42 through the resistance of the myocardium. The average resistance of the myocardium across internally placed discharge electrodes averages 50 ohms. This provides a time constant of approximately 7 milliseconds for an equivalent capacitance of 140 $\mu$F, as is typical for capacitors 40 and 42. Truncation of the capacitive discharge at the time constant results in roughly 250 volts at time point 50 across the discharge electrodes when the defibrillating discharge is truncated by closing SCR 46 to starve SCR 44. After time point 50, the capacitor charge is shunted through SCR 46 truncating the curve as seen in FIG. 2. FIG. 3 depicts the current seen at the cardiac electrodes and corresponds to the voltage discharge depicted in FIG. 2. Peak current flow 52 represents the initial peak current and is seen to decay in an exponential fashion to current flow 54 at time of truncation some 7 milliseconds later. The terminal current is about 5 amperes at time of truncation.

Figure 4:
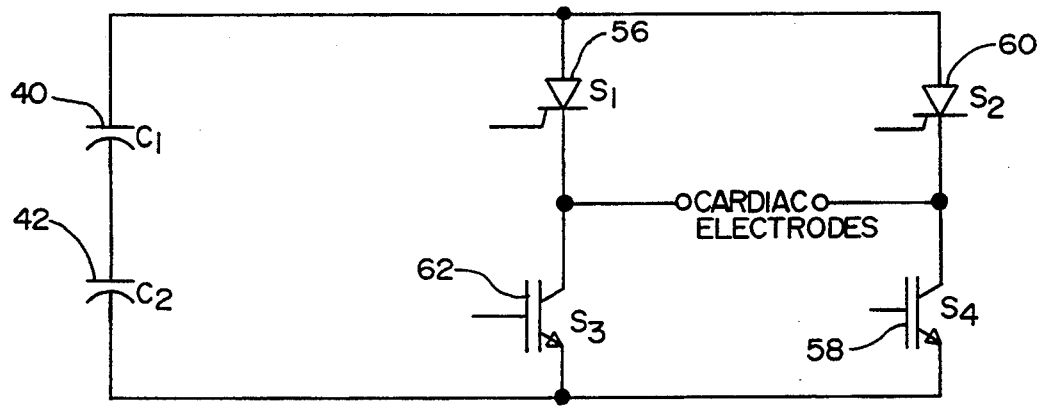
FIG. 4 is a simplified electrical schematic of an ICD using an H bridge output circuit to the discharge electrodes in an existing ICD system.

Numerous studies on the electrophysiology of defibrillation have revealed that a fibrillating myocardium is more responsive to what is now termed a biphasic countershock discharge. This is in contrast to the Schuder circuit of FIG. 1 which produces a monophasic countershock discharge as depicted in FIG. 2. FIG. 4 represents a simplistic circuit depiction of a bridge circuit using solid state switches to give rise to an H-bridge configuration allowing for reversal of polarity at the cardiac electrodes. As with FIG. 1, control circuitry 32 responds to a sensing signal (not shown) to detect the presence of a cardiac arrhythmia, and, in response, selectively controls the charging and discharging of capacitors 40 and 42. As shown in FIG. 4, high voltage electrolytic capacitors 40 and 42 are each charged to approximately 375 volts by split winding transformer 36 from battery source 36. A biphasic defibrillation countershock is initiated by closing SCR 56 and metal oxide semiconductor field effect transistor (MOSFET) 58. After a predetermined period of time of discharge across cardiac electrodes 38, MOSFET 58 is opened which starves the current across SCR 56 turning it off as well. The defibrillation countershock is completed by then closing SCR 60 and MOSFET 62 effectively reversing the polarity across cardiac electrodes 38. The countershock is truncated by opening MOSFET 62 which also in effect starves the current across SCR 60 allowing it to open as well. This configuration allows for preservation of the terminal portion of energy still stored on capacitors 40 and 42 to remain there if needed for subsequent shocks.

Figure 5:
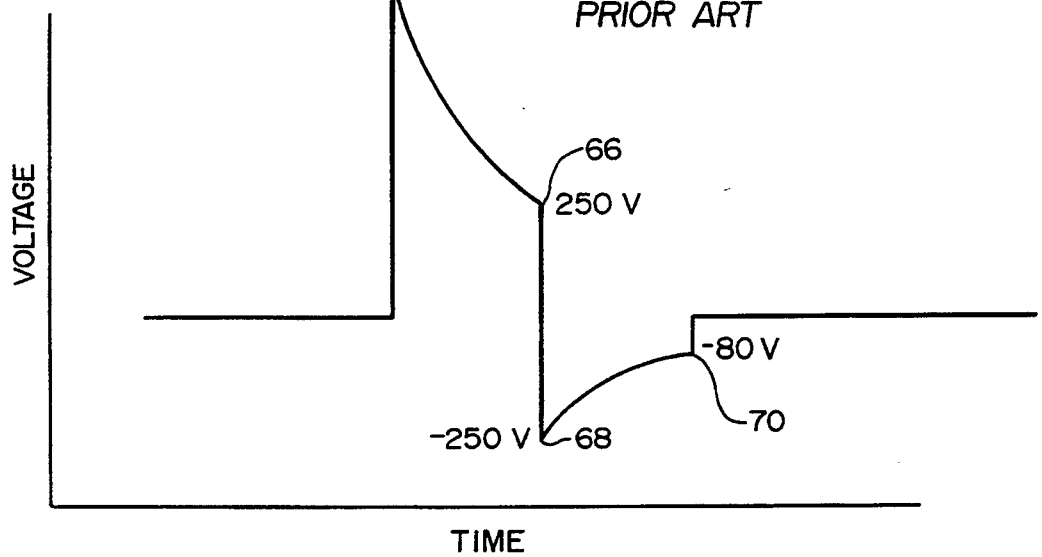
FIG. 5 is a graph depicting the voltage discharge for a typical biphasic countershock pulse generated by the circuit shown in FIG. 4.

FIG. 5 represents a graphic representation of the voltage versus time output for a biphasic discharge. Time point 64 represents the initial 750 volt charge on capacitors 40 and 42. When SCR 56 and MOSFET 58 are closed there begins an exponential discharge of capacitors 40 and 42 as noted by the curve as it approaches time point 66. At time point 66 there is a near instantaneous reversal of polarity by following the above noted sequence reversing the polarity from approximately 250 volts to −250 volts in relation to the cardiac electrodes 38 as noted at point 68. The second portion of the biphasic discharge is then completed ending with truncation occurring at time point 70 with a remaining −80 volts across the capacitors 40 and 42 as measured in relationship to the polarity of cardiac electrodes 38.

FIG. 1 and FIG. 4 represent the classical circuit designs for conventional ICD systems. In general, and for reference throughout this application, cardiac electrode polarity and phase will be understood by reference to a discharge control circuit which may include either of the classic circuit configurations, but is not intended to be limited to them.

In the co-pending application entitled IMPLANTABLE CARDIOVERTER DEFIBRILLATOR EMPLOYING POLYMER FILM CAPACITORS, polymer thin film capacitors having capacitances of less than about 80 $\mu$F, and hence, time constants of less than about 4 milliseconds are proposed as an alternative to the pair of electrolytic capacitors which are used in existing ICD systems. Electrolytic capacitors are used in existing ICD systems to take advantage of their capacitance to volume or ratio, known as their energy density value. Electrolytic capacitors are capable of storing approximately 1.77 joules per cc of volume. This capacity is predicated on the electrolytic capacitor in a cylindrical shape. When the inefficiencies of putting a cylindrical shape into a generally rectangular space are taken into account, the effective energy density value decreases to about 1.33 joules/cc for aluminum oxide electrolytic capacitors as used within an ICD system. Unfortunately, due to the nature of the aluminum oxide dielectric, electrolytic capacitors are limited to charging voltages of about 375 volts before break down begins to occur and the capacitors begin to suffer from significant current leakage.

By comparison, newer polymer films are being developed which are actually more effective at higher charging voltages, and which have significantly improved mechanical strength and durabilities. In this way these films are capable of being consistently rolled out to thinner dimensions. Due to the nature of polymer films the storage to volume ratio remains constant whether formed as a cylinder or as a flattened device. Thus, there is no decrease in the packaging efficiency when converting from a cylindrical shape to a more flattened packaging as is incurred with electrolytic capacitors.

Figure 6:
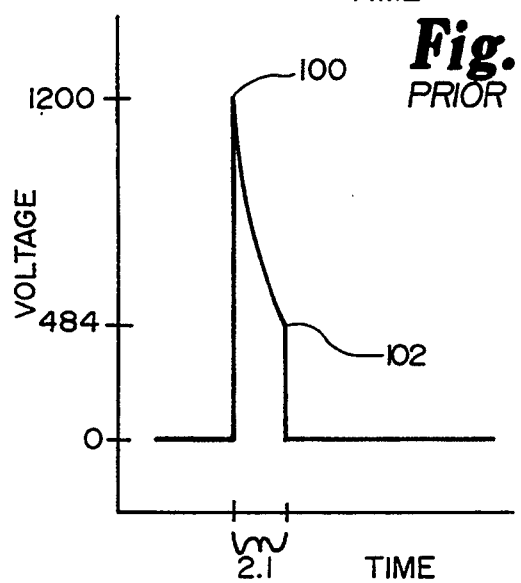
FIG. 6 is a graph depicting a voltage output for a polymer film capacitor.

Both the monophasic waveform of FIG. 2 and the biphasic waveform of FIG. 5 represent the present art taking advantage of dual electrolytic capacitors with an equivalent capacitance of approximately 140 $\mu$F. Contrast this to the graph shown in FIG. 6 which represents a voltage versus time discharge of a system if it were to use a 42 $\mu$F polymer film capacitor charged to 1,200 volts initially. Such a capacitor would store 30 joules of energy and in one time constant of 2.1 millisecond deliver a little over 26 of those joules across cardiac electrodes. The amount of energy delivered by such a system is sufficient to accomplish defibrillation. In terms of the chronaxie, however, it is an inefficient utilization of the energy because the duration of the discharge is significantly shortened.

Discharge duration can be increased by increasing the time constant. This is achieved by either increasing the resistance or increasing the capacitance. Increasing the resistance introduces a lossy element which decreases efficiency. Increasing the capacitance can be accomplished by increasing the surface area of the capacitor, but this increases capacitor volume. Alternatively, one could decrease the dielectric thickness, but polymer films can be only so thin. Consequently, a trade off must be made by using as thin a dielectric as possible for a reasonable charge voltage and to look elsewhere to increase the countershock duration.

Figure 7:
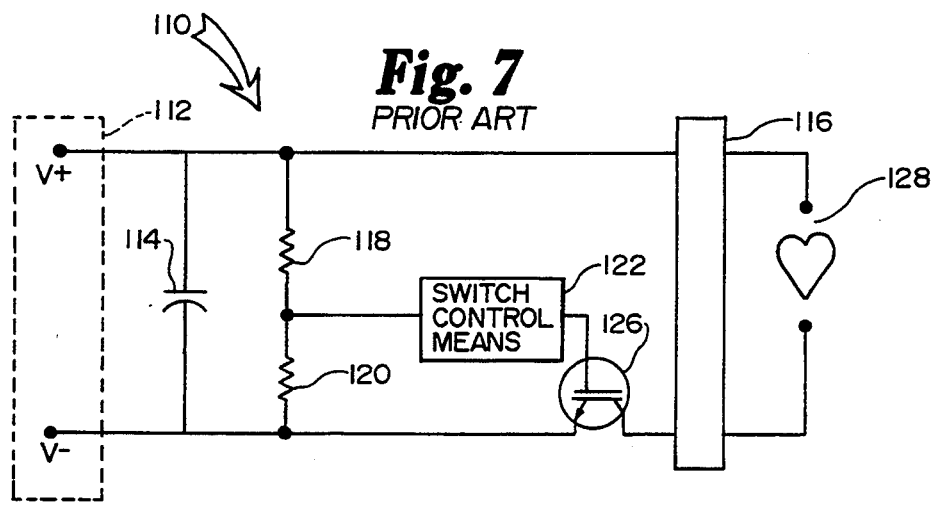
FIG. 7 is an electrical schematic diagram of an embodiment of the present invention.

The effective duration period can be lengthened by periodic and rapid interruption of the discharge current across the cardiac electrodes. FIG. 7 depicts an embodiment of the present invention comprising a power source 112, a polymer film capacitor 114, a resistive divider comprised of a resistor 118 and a resistor 120 connected in parallel with capacitor 114, a discharge control means 116 for controlling the polarity of the discharge pulse to cardiac electrodes 128, a switch control means 122 electrically connected between resistor 118 and resistor 120 and an opposite end connected to the gate of a power FET switch 126 with source and drain connected in series between discharge control means 116 and capacitor 114.

The concept of opening and closing switches to control discharge of energy flow to the cardiac electrodes is not new in the area of ICD systems. To date, however, there has been no teaching or suggestion that any of these switching techniques could be used to alter the natural characteristics of the capacitor system of the ICD system. Nor has there been any teaching or suggestion that these switching techniques could extend the duration of a countershock discharge and thereby enable the ICD system to make use of a short tau capacitor. Consequently, while these references are presented as background, they are not considered to be pertinent to the claimed invention of this application because they simply do not address the issue of how a switching circuit might affect the natural discharge duration of the capacitor system of an ICD system.

In U.S. Pat. No. 4,768,512 issued Sep. 6, 1988 to Imran, a switch is disclosed in series between the high voltage capacitors and the switch control circuitry that is open and closed at a frequency determined by a clock. With every clock cycle the circuit is opened alternately with closure such that there ends up being a 50% duty cycle of the discharge on the cardiac electrodes. Half of the time the high voltage capacitors are discharging through the cardiac electrodes and the other half of the time voltage drops to zero across the cardiac electrodes.

As disclosed, Imran's purpose behind this high frequency pulsing is to distribute the energy throughout the heart in an attempt to alter the impedance encountered by the output of the ICD system, and thereby lower the energy requirements necessary to effect cardioversion. In essence, the Imran patent is a Schuder circuit utilizing a non-variable clock driven switch. In the specification, Imran does not suggest what effect, if any, this system will have on capacitor design. The only information about the capacitor system disclosed in the Imran specification is contained in a patent which Imran references for the design of the inverter circuit. That patent discloses that the capacitor is to be charged to about 600 volts. When the drawings are examined, however, Imran actually teaches away from the present invention by teaching in the drawings that the chopped pulse created by the 50% duty cycle is to be identical in overall duration to that of a naturally decaying capacitive discharge.

Another example of a switching circuit used to control the discharge output is U.S. Pat. No. 5,184,616 issued Feb. 9, 1993 to Weiss which discloses a microprocessor that controls a high voltage circuit by a shock control pulse sequence, the output of which is then smoothed by a filter circuit. The shock control pulses control the switches of a standard H-bridge circuit that generates the input to the filter circuit. The only reference to the specifications for the high voltage defibrillation capacitor in Wiess is that the capacitor is 600 volts. There is no information provided as to the overall pulse duration of a defibrillation countershock. The only indication as to the timing of Wiess is that the individual pulses of the shock control pulse sequence are on the order of hundreds of microseconds.

One of the problems with the switching circuit disclosed by Weiss is that the size of the filter circuit which is called out, but not specifically discussed, will be proportional to the energy of the pulse. While such a filter circuit might be practical for an implantable device in order to smooth the output of a pacing pulse having an output energy of several microjoules, a filter circuit would not be practical for an implantable device in order to smooth the output of a defibrillation countershock having an output energy of up to 30 joules or more.

In both Imran and Wiess, it will be seen that there is simply no need or suggestion to employ the duration extention techniques taught by the present invention. In each case, the capacitor system is charged to about 600 volts. According to Eq. (2), for a maximum defibrillation countershock of about 35 joules, the effective capacitance value C of the capacitors in both Imran and Wiess would be about 195 $\mu F$. Solving for the time constant $\tau$ from Eq. (4) yields a time constant of almost 10 ms. Because 10 ms is almost three times the average chronaxie value, the effective of the defibrillation countershock is not affected by the discharge duration and there is simply never a need for the outputs of Imran or Wiess to be extended. In contrast, the present invention utilizes short tau capacitors which are charged to voltages much higher than 600 volts. Consequently, the time constant $\tau$ is substantially at or below the defibrillation chronaxie value of a human patient and, as previously discussed, the effectiveness of the defibrillation countershock is affected by the discharge duration.

Unlike the device described by the Iraran patent which essentially is a Schuder circuit, or the the device described by the Wiess patent which is not practical for cardioversion or defibrillation countershock, the preferred embodiment of the present embodiment depicted in FIG. 7 utilizes switch control means 122 deriving its control based on the voltage perceived across resistors 118 and 120. In addition, control means 122 does not truncate the countershock output at about the time constant $\tau$ as is typical for existing ICD systems. Rather, the duration of the defibrillation countershock is extended to substantially at or above the defibrillation chronaxie value of a human patient.

Figure 8:
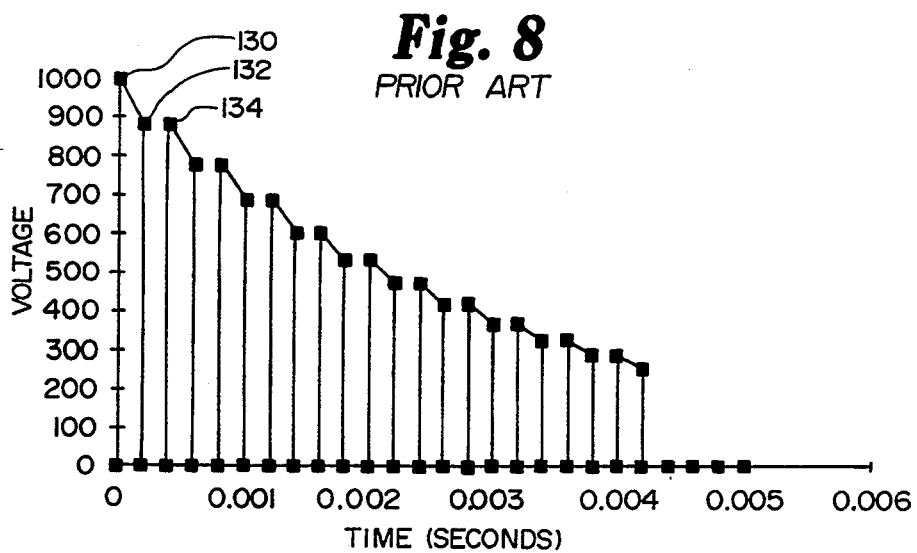
FIG. 8 is a graphic representation of the voltage discharge characteristics for a 50—50 duty cycle as found in the prior art.

FIG. 8 is a graphic representation of the discharge output that would be expected from a 34 μF polymer film capacitor initially charged to 1,000 volts and utilizing the clock controlled to a 50% duty cycle to produce an output that is not truncated at the time point where a natural decaying exponential would otherwise be truncated. As shown in FIG. 8, the cycle frequency is approximately 5,000 Hertz. Beginning with time point 130, initial voltage across the capacitor is 1,000 volts which exponentially decays to time point 132 at which time the clock cycles and turns off the discharge pulse and remains off for the same amount of time as from time point 130 to time point 132 to time point 134. At time point 134, the clock of a 50% duty cycle circuit would cycle the discharge back on and the voltage would jump back up to the voltage that was still remaining on the capacitor when it had been cycled off at time point 132. As can be seen in FIG. 8, by not truncating the output at the point in time where a natural expontentially decaying pulse would have been truncated, this embodiment can generate a generally exponential decaying output that has extended the discharge duration by approximately a factor of two.

Unlike the devices in Imran or Wiess, the present embodiment also takes into account the voltage charge developed across the myocardial cell membrane and the Helmholtz double layer capacitor between the cardiac discharge electrodes. The myocardial cell transmembrane capacitance has a time constant that varies from 100 μs to 20 ms, depending upon the type of cell and the measurement technique used. The discharge electrodes themselves form a capacitor called a Helmholz double layer capacitor. The importance of utilizing this inherent characteristic of the discharge electrodes is apparent by comparison of the result of an Imran circuit versus the present invention. For purposes of this comparison, the effect of the cellular transmembrane capacitance and the Helmholz double layer capacitor at the discharge electrodes will be combined into an equivalent circuit having an effective time constant of approximately 300 microseconds which will be referred to as the cardiac capacitance.

The 300 microsecond time constant is an approximation of the electrode time constant which varies significantly with the electrode type, size and implantation location, as well as voltage, and the myocardial cell time constant. It should be noted that, although the 300 microsecond time constant is used in describing the preferred embodiment, the present invention is not limited to this value, but is merely using this value to illustrate the smoothing seen from the electrodes and the myocardial cells. For most ICD systems, the electrode time constant will be much less than 300 microseconds, but the myocardial cell time constant is much greater than 300 microseconds. Thus, the 300 microsecond time constant is used as an illustrative approximation for both. The resulting voltages (after the smoothing of the time constant) will be referred to as the cardiac voltage.

Figure 9:
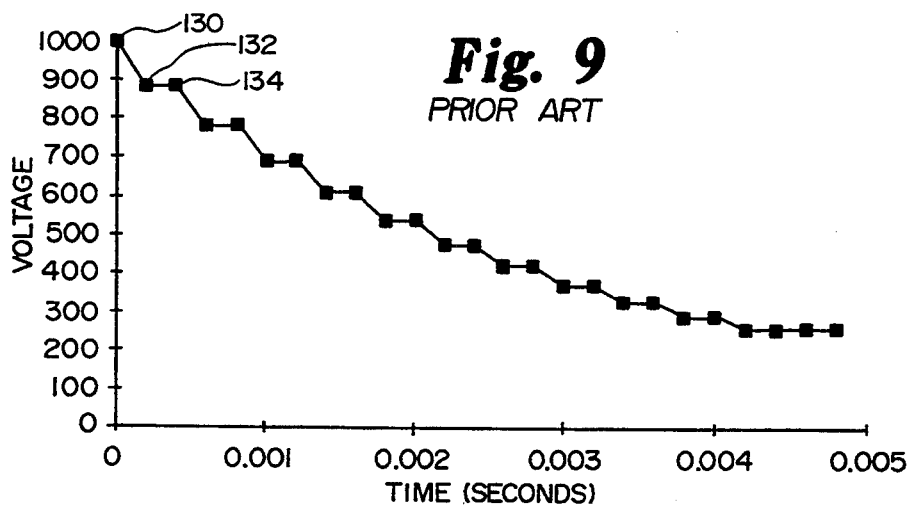
FIG. 9 is a graphic representation of the voltage seen across a capacitor being discharged as depicted in FIG. 8.

FIG. 9 depicts a graphic representation of the voltage versus time as seen across the polymer film capacitor. As noted at time point 130, there is an initial charge of 1,000 volts which exponentially decays to point 132 when the clock cycles the output circuit off. Thus between time point 132 and time point 134 the charge across the capacitor remains constant until the clock cycles the output circuit back on allowing for the discharge of the capacitor.

Figure 10:
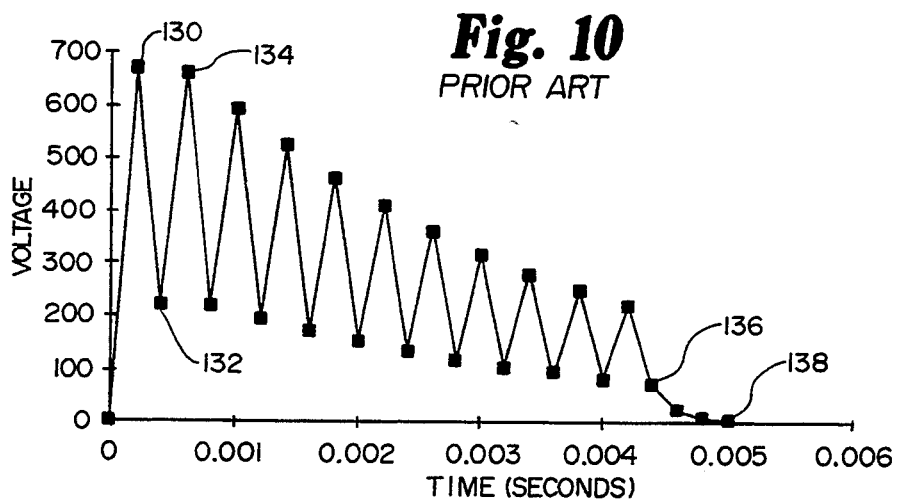
FIG. 10 is a graphic representation of the cardiac voltage according to the circumstances depicted in FIG. 8.

The real significance of this effect is evident in FIG. 10 depicting the graphic representation of the voltage across the discharge electrodes for the same time periods. When one takes into account the cardiac capacitance, the actual cardiac voltage rises to about 670 arbitrary voltage units by the time the first cycle ends at time point 130. As the clock cycles the output circuit off, the voltage decays to just over 200 volts by time point 132. When the clock recycles the output circuit back on between time point 132 and point 134 the cardiac voltage rises once more. By time point 136 when the clock cycles the output circuit off for the final time, there is a rapid decay of the voltage to time point 138.

The waveform shown in FIG. 10 is of a significantly greater duration than the time constant this 34 μF capacitor would allow. Thus, it is a more efficient waveform for defibrillation having extended the time of discharge duration from a time constant of 1.7 milliseconds out to a 4.2 millisecond defibrillation pulse duration. However, it is still not as efficient as is possible as the waveform is rather far removed from the ideal rectangular waveform. It is well known from theoretical and animal studies that a rectangular waveform or a good approximation thereof, is more efficient than a rapidly decaying waveform.

In a preferred embodiment of this invention, the intermittent interruption of the discharge output is asynchronous and variable so as to greatly increase the efficiency of delivering the energy from a short tau capacitor by delivering a wider pulse which more closely approximates a rectangular wave. To accomplish this, the present invention as depicted in FIG. 7 utilizes a control means which is able to estimate the voltage effectively seen after the smoothing effect of the cardiac capacitance.

Figure 11:
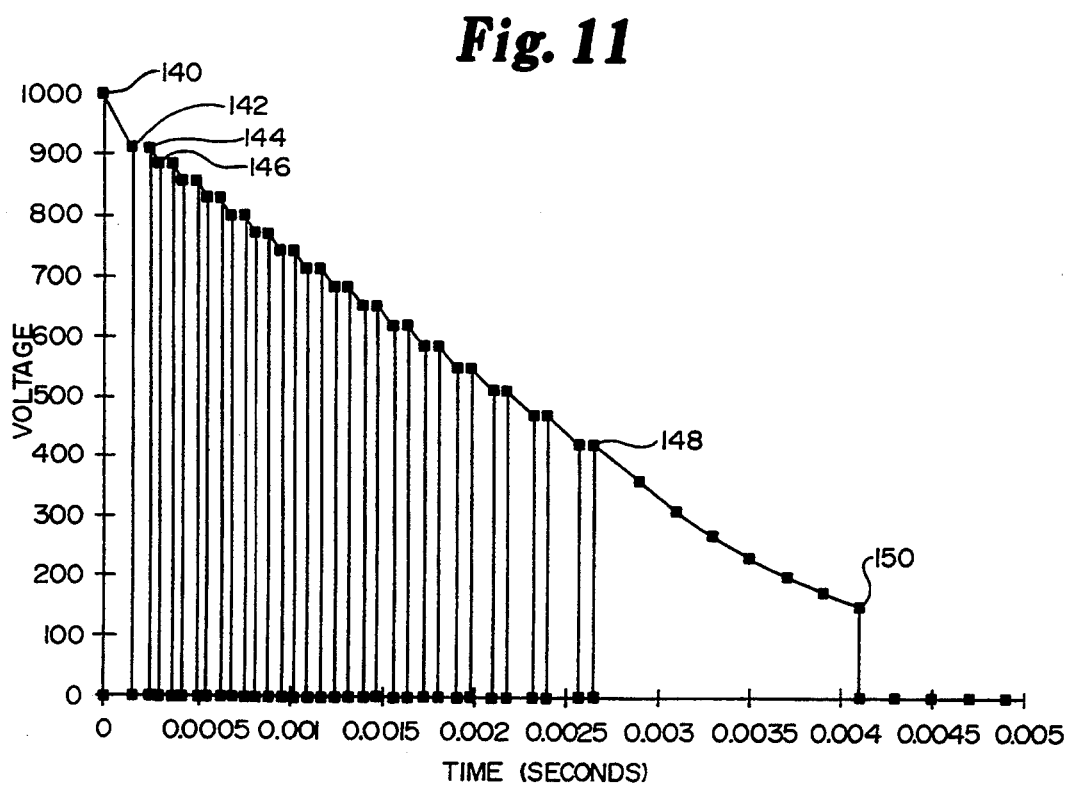
FIG. 11 is a graphic representation of the voltage discharge according to an embodiment of the present invention ignoring the cardiac capacitance.

FIG. 11 depicts a graphic representation of the output of the circuit disclosed in FIG. 7 for voltage versus time assuming no cardiac capacitance. The cardiac voltage is shown for purposes of representation in scaled or arbitrary voltages units. Once again, a 34 μF polymer film capacitor is used, having been initially charged to only 1,000 volts. From time point 140 to time point 142 there is an exponential decay down to approximately 910 volts, at which time, switch control means 122 turns off switch 126. Between time point 142 and point 144 there is no discharge and as the voltage drops to a preselected level as detected by switch control means at resistor dividers resistor 118 and resistor 120, switch control means can reactivate switch 126 showing the rise in voltage at point 144. The duration of discharge from time point 144 to time point 146 is considerably shorter than the discharge period from time point 140 to time point 142 because it takes considerably less time to take the voltage from 300 back up to 400 than it did to take it from zero to 400 as it had to during the time period between time point 140 and time point 142.

As can be seen in FIG. 11, there is a more linear discharge between time point 146 and time point 148. At time point 148 the charge across capacitor 114 has fallen to 400 volts and can no longer maintain a 400 volt cardiac potential and therefore switch control means will then cycle switch 126 on until terminal truncation at time point 150. From time point 148 to time point 150 there is exponential decay of capacitor 114. Thus, capacitor 114 has been discharged from 1,000 volts to just under 200 volts in just over 4 milliseconds instead of just under 2 milliseconds as would have happened if capacitor 114 had been allowed to discharge continuously.

Therefore the present invention, by utilizing a variable duty cycle based on actual voltages, has achieved an output efficiently extending the discharge duration.

Figure 12:
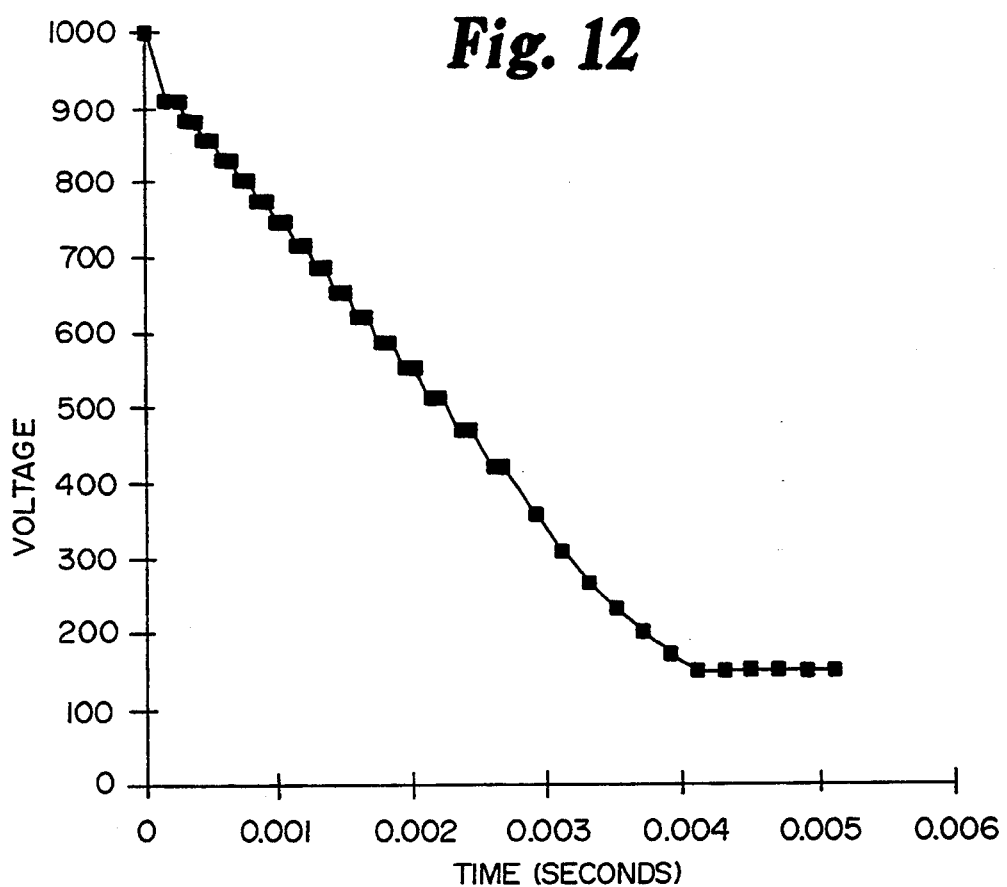
FIG. 12 is a graphic representation of the voltage discharge across a high voltage capacitor used in an embodiment of the present invention.
Figure 13:
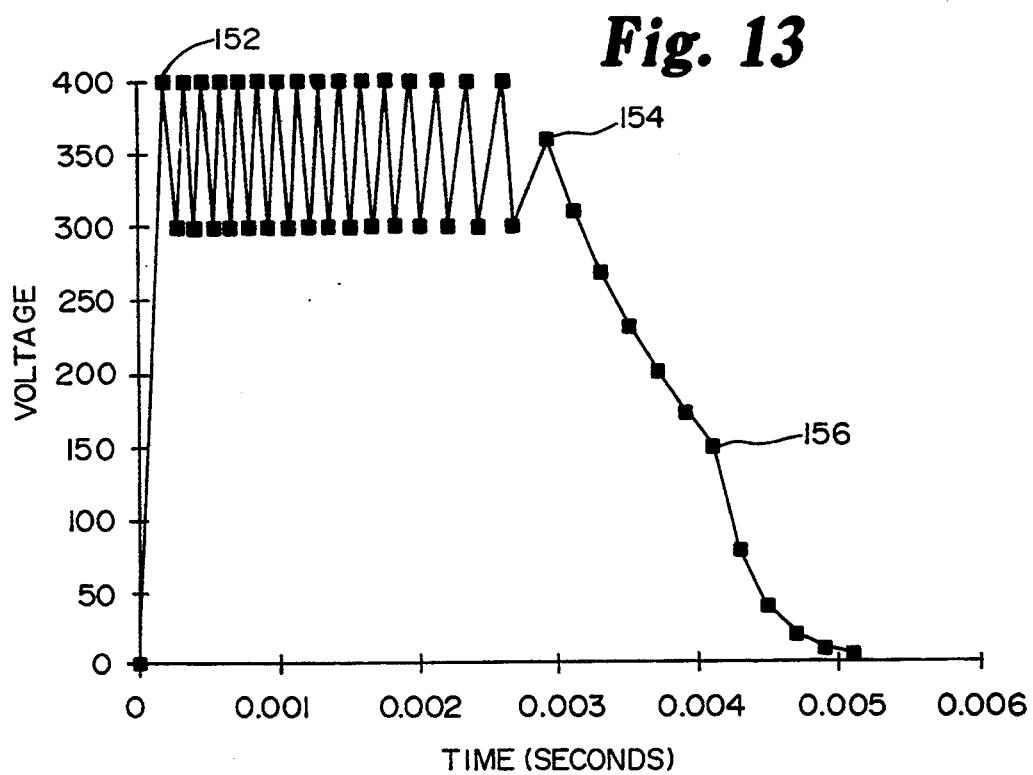
FIG. 13 is a graphic representation of the cardiac voltage of an embodiment of the present invention.

FIG. 12 is a graph depicting the voltage as seen across the capacitor corresponding to the discharge pattern as shown in FIG. 11. As shown in FIG. 12 the asynchronous discharge of the 34 $\mu$F capacitor yields a more uniform linear decay of the polymer film capacitor. By comparison, FIG. 13 represents the voltage which would be seen in the heart demonstrating the asynchronous cycling of switch 126 on and off based upon the voltage ranging from 400-300 volts. As shown in FIG. 13, from time point 152 to time point 156 the waveform very nearly approximates a rectangular wave. From time point 154 to time point 156 the discharge follows the exponential decay curve of a 34 $\mu$F capacitor and at time of discharge truncation at time point 156 the remaining curve represents the exponential decay for the cardiac capacitance.

Figure 14:
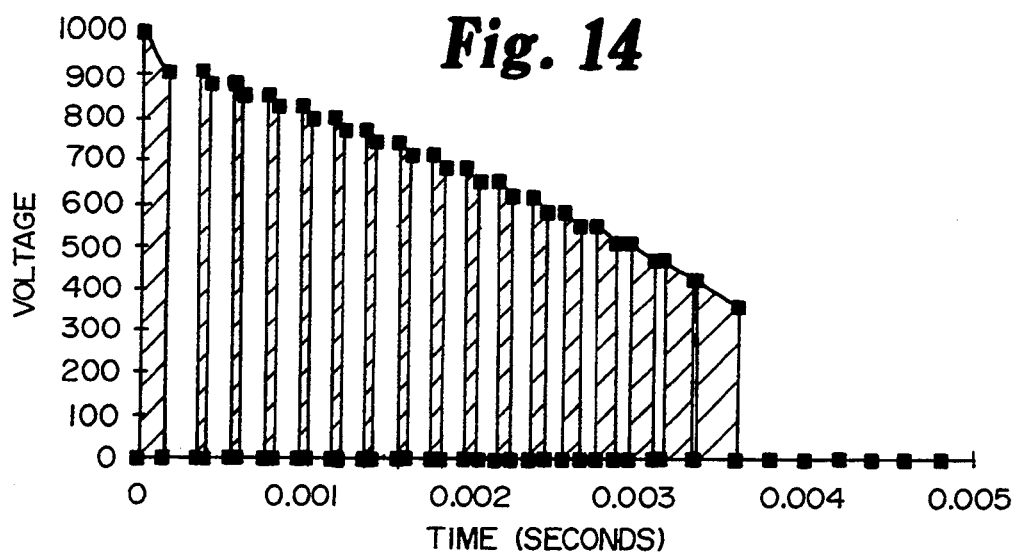
FIG. 14 is a graphic representation of the voltage discharge of an alternative embodiment of the present invention ignoring the cardiac capacitance.
Figure 15:
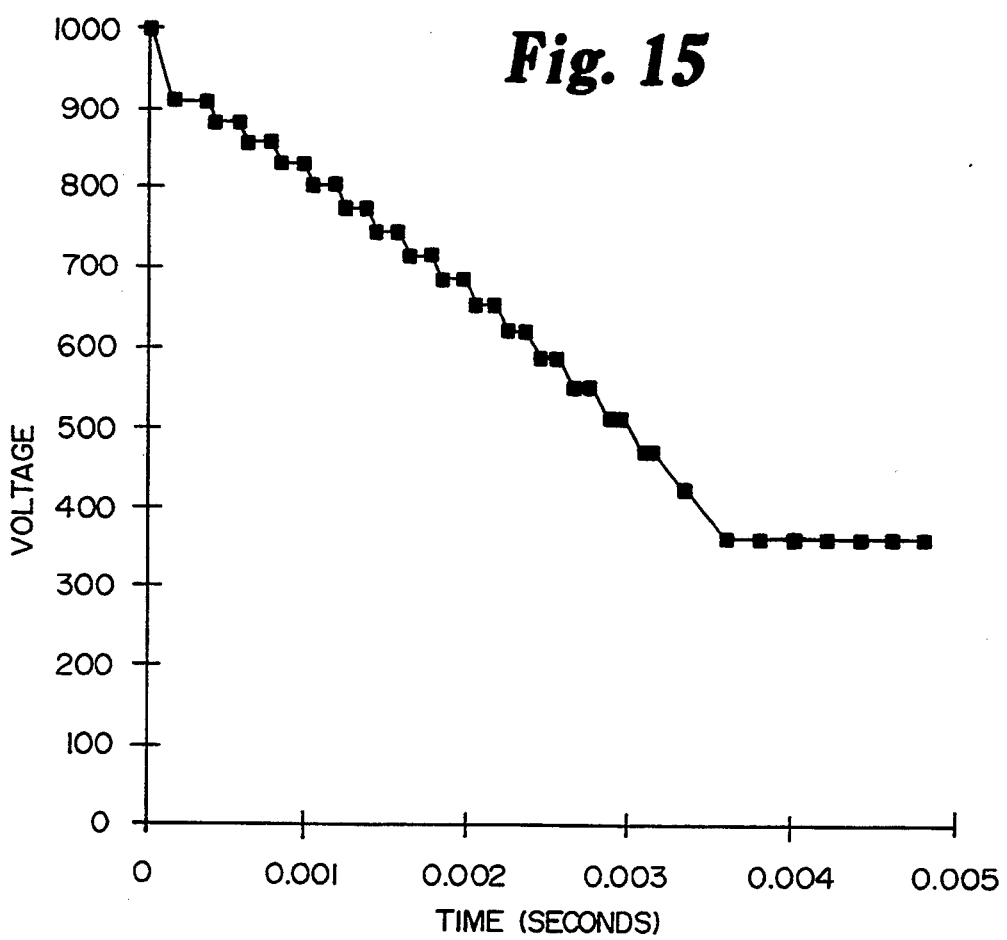
FIG. 15 is a graphic representation of the voltage across a high voltage capacitor in an alternate embodiment of the present invention.

An alternative embodiment for a switch control means 122 would be to fix the frequency by which switch 126 is turned on, but vary the duty cycle of switch 126. The duty cycle is the percentage of time that the output is on. This alternative approach is represented in FIG. 14 depicting a graph of voltage versus time for voltage seen ignoring the cardiac capacitance. As shown, switch 126 is pulsed on at a fixed frequency but is switched off in an asynchronous fashion gradually increasing the duty cycle for the discharge pulse. The percentage of time that the switch is on during its pulsing period gradually increases to allow for maintenance of a more constant effective smoothed voltage after the smoothing effect of the cardiac capacitance. FIG. 15 depicts the voltage versus time for the voltage across the polymer film capacitor which is again a 34 $\mu$F polymer film capacitor charged to 1,000 volts initially.

Figure 16:
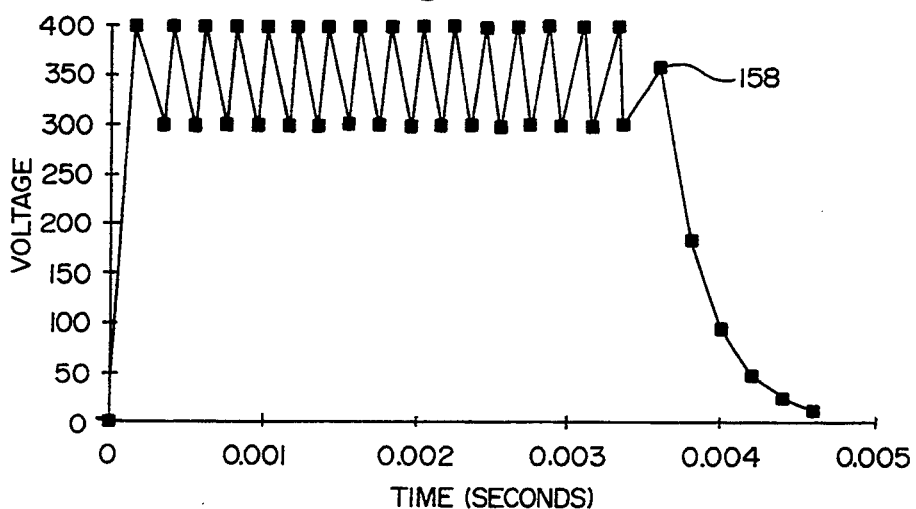
FIG. 16 is a graphic representation of the cardiac voltage of an alternate embodiment of the present invention.

This variable duty cycle period yields a graph as depicted in FIG. 16 showing the effective voltage as a function of time due to the smoothing effect of the cardiac capacitance. As switch control means 122 varies the duty cycle and responds to maintaining the discharge electrodes between 300 and 400 volts, a discharge pulse of roughly rectangular shape is obtained for approximately 3.5 milliseconds out to time period 158 at which time the polymer film voltage falls below the ability to recharge the discharge electrods to 400 volts and switch control means turns on switch 126 until the defibrillation discharge is truncated.

Figure 17:
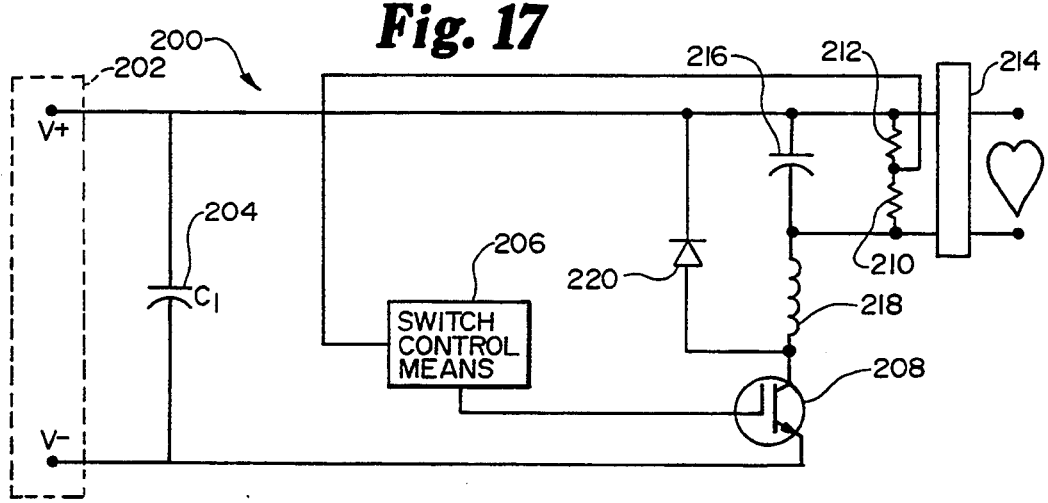
FIG. 17 is an electrical schematic representation of an alternative embodiment of the present invention.

Approximation of a nearly rectangular wave discharge pulse as seen in FIG. 16, or for the first phase of the biphasic waveform, can also be produced by incorporating a low pass filter circuit into the output circuit of an ICD. An additional embodiment of such a circuit is depicted in FIG. 17 as system 200 comprising a power supply 202, a single polymer film capacitor 204, a switch control means 206, a switch 208, a resistive divider with resistors 210 and 212, discharge control 214, a capacitor 216 in parallel with the resistive divider resistors 212 and 210 and in series with inductor 218 and switch 208, and diode 220 connected in parallel to capacitor 216 and inductor 218. Inductor 218 and capacitor 216 serve to form an efficient low pass filter of minimal energy loss. The resistor divider resistors 210 and 212 are located directly in the output circuit. Inductor 218 and capacitor 216 are chosen in such a fashion as to approximate the characteristics of the cardiac cell membranes or electrodes. Diode 220 couples the energy stored in inductor 218 back to the output path after each time switch 208 is switched off. Using the techniques described and depicted in FIGS. 14, 15, and 16 and in which the duty cycle varies to maintain a discharge electrode potential between 300 and 400 volts, the circuit depicted in system 200 as shown in FIG. 17 may be used to generate a highly efficient nearly rectangular biphasic waveform.

Unlike the filter circuit of Wiess, because the characteristics of inductor 218 and capacitor 216 are chosen to approximate the cardiac cell membrane and discharge electrodes, the overall size of these components is fairly nominal. Representative values for inductor 218 are 500 $\mu$H and for capacitor 216 are 0.1 $\mu$F. In a preferred embodiment, inductor 218 is incorporated as part of a telemetry loop antenna within the ICD system to double up on the functionality of components, and, thereby save space within the ICD system. Obviously, such a design would need to insure that the fine wire used in the loop antenna was not damaged by the high current of a defibrillation countershock, and that the magnetic fields generated by pulsing a current through the loop antenna would not reset or otherwise affect any of the other circuitry within the ICD system.

Figure 18:
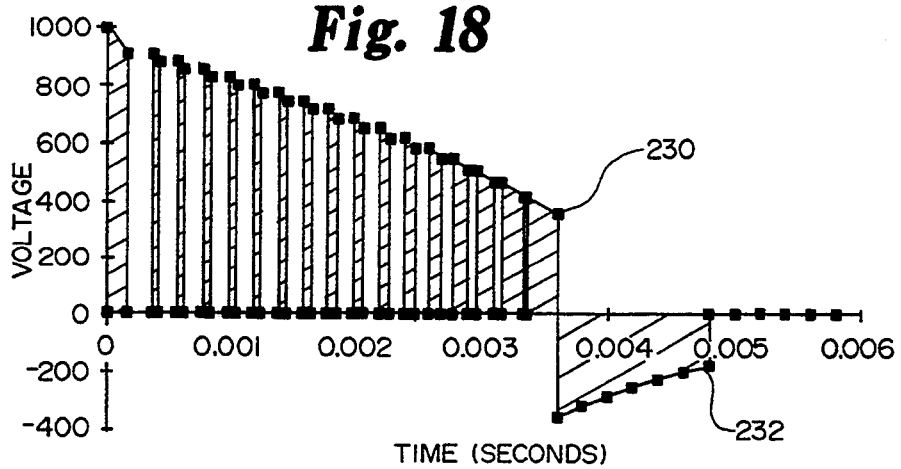
FIG. 18 is a graphic representation of the voltage output (before filtering) as delivered in a biphasic form by an alternate embodiment of the present invention of FIG. 17.

This biphasic waveform is shown in FIG. 18 (before the filter) again using a 34 $\mu$F polymer film capacitor charged to 1,000 volts. As shown in FIG. 18, the duty time increases with each cycle of switch 208 as controlled by switch control means 206. Switch control means monitors the voltage as derived by the resistor divider resistors 212 and 210 which monitor the voltage change across capacitor 216 in conjunction with inductor 218 to maintain the voltage across capacitor 216 to between 300 and 400 volts. In FIG. 18 at time point 230, discharge control means 214 reverses the polarity of the discharge electrodes and capacitor 204 is allowed to discharge in a reversed polarity fashion to complete the biphasic defibrillation countershock by time period 232. Note that at time point 230 the voltage across capacitor 204 is at 400 volts such that when polarity reversal is accomplished by discharge means 214, capacitor 204 is allowed to discharge continuously by switch control means 206 keeping switch 208 in the on position until final termination of the defibrillation countershock at time period 232.

Figure 19:
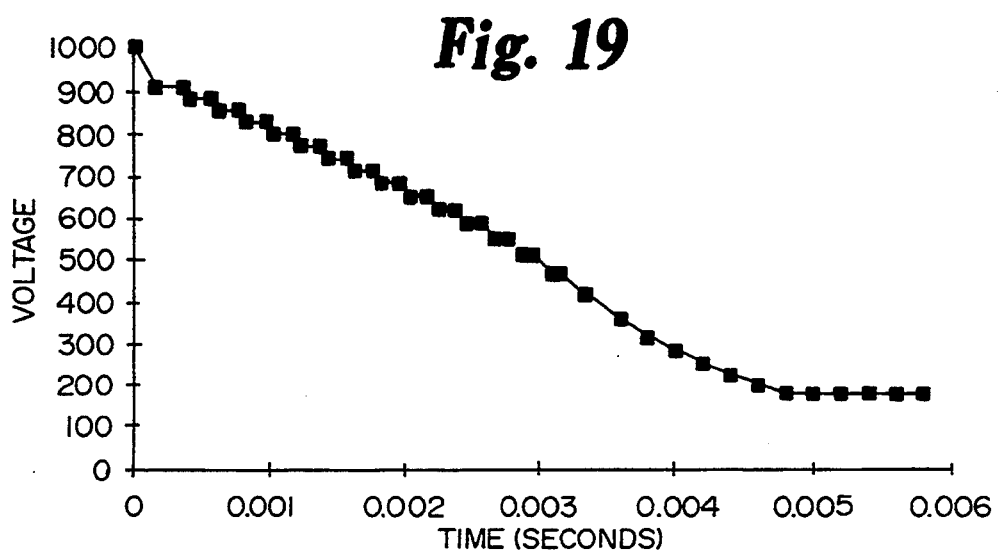
FIG. 19 is a graphic representation of the voltage across the high voltage capacitor of an alternate embodiment of the present invention as depicted in FIG. 17.

FIG. 19 depicts the voltage versus time graph for voltage across capacitor 204. Note at 3.5 milliseconds there is no polarity reversal since this is a function of discharge means 214.

Figure 20:
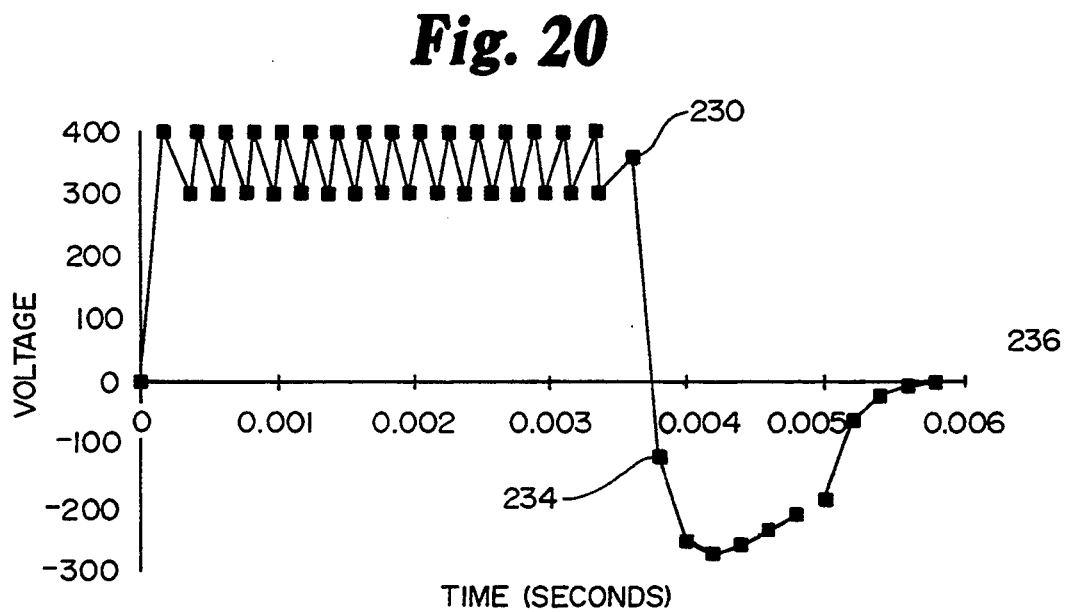
FIG. 20 is a graphic representation of the cardiac voltage of an alternate embodiment of the present invention as depicted in FIG. 19.

FIG. 20 shows a voltage versus time graph for the cardiac voltage demonstrating the nearly rectangular discharge waveform accomplished by maintaining the voltage across capacitor 216 between 300 and 400 volts for the first portion of the biphasic discharge. At time point 230, with discharge polarity reversal accomplished by discharge means 214, capacitor 204 is allowed to discharge continuously. From time point 234 until time point 236 the voltage potential across a discharge electrode follows the gradual sloping discharge curve as modified by the effects of capacitor 216 and inductor 218 on the discharge characteristics of capacitor 204. Overall effect is to achieve a biphasic defibrillation countershock pulse of very nearly rectangular proportions in both phases of the biphasic countershock.

A 34 $\mu$F polymer film capacitor charged to 1,000 volts will store 17 joules of energy. This capacitor will occupy 8.5 cc of volume and have a time constant of 1.7 milliseconds. The present invention through its various embodiments achieves a nearly rectangular discharge waveform using this small capacitor. A 34 μF polymer film capacitor can deliver 16.3 joules of energy through the myocardium while maintaining an average 7 amperes of current during the first phase lasting approximately 3.5 milliseconds. Thus, as embodied, a single 34 μF microfilm capacitor charged to only 1,000 volts is sufficient to generate an efficient defibrillation countershock pulse. A present invention utilizing a 42 μF polymer film capacitor will be able to store 30 joules of energy in a 15 cc volume and deliver 26 joules as a countershock pulse in a monophasic or biphasic fashion and still occupy a far smaller volume than present day ICDs utilizing electrolytic capacitors.

The present invention provides for significantly greater efficiency for an ICD in terms of total capacitor size and in achieving a more desirable waveform.

We claim:

1. An implantable cardioverter defibrillator apparatus electrically connected to two or more implantable discharge electrodes adapted to be located in a human patient for treating cardiac dysrhythmias, the apparatus comprising:
   a) sensing means for sensing cardiac dysrhythmias;
   b) charge storage means for storing an electric charge to be delivered to the two or more implanted electrodes, the charge storage means having a charge storage means capacitance value that is less than about 60 μF and the charge storage means and the implanted electrodes having a time constant defined by an inter-electrode resistance value multiplied by the charge storage means capacitance value that is substantially at or below a maximum defibrillation chronaxie duration for the human patient heart of about 5 milliseconds:
   c) power source means for charging the charge storage means;
   d) discharge means for selectively discharging the charge storage means through the two or more implanted electrodes in response to the sensing of a cardiac dysrhythmia to deliver the electrical charge as a cardioversion countershock; and
   e) control means electrically connected between the charge storage means and the discharge means for intermittently interrupting the discharge of the charge storage means to effectively lengthen the time of the cardioversion countershock substantially at or greater than the maximum defibrillation chronaxie duration of the human patient heart.

2. The apparatus of claim 1 wherein the control means comprises:
   a resistive divider comprised of a first resistor and a second resistor connected in parallel with the charge storage means;
   a power transistor connected in series between the discharge means and the charge storage means; and
   a switch control means electrically connected between the first and second resistors and to power transistor for intermittently interrupting the discharge of the charge storage means.

3. The apparatus of claim 1 wherein the control means is operated to asynchronously interrupt the discharge of the charge storage means in response to an estimated voltage as seen by the discharge electrodes.

4. An improved implantable cardioverter defibrillator apparatus electrically connected to two or more implantable discharge electrodes adapted to be located in a human patient for treating cardiac dysrhythmias, the apparatus having a sensing means for sensing a cardiac dysrhythmia, charge storage means for storing an electrical charge, power source means for charging the charge storage means, discharge means for selectively discharging the charge storage means into the two or more implanted discharge electrodes to deliver the electrical charge as a cardioversion countershock, the improvement comprising:
   a) charge storage means having a high voltage capacitance storage means with a characteristic time constant of less than about 3 milliseconds; and
   b) control means electrically connected between the charge storage means and the discharge means for periodically interrupting the output of the charge storage means to the discharge means to effectively lengthen the discharge time of the cardioversion countershock to a duration appropriate for the treatment desired for the cardiac dysrhythmia sensed.

5. The improved apparatus of claim 4 wherein the high voltage capacitance storage means has a charge storage capacitance value that is less than about 60 μF.

6. A method for operating an implantable cardioverter defibrillator device electrically connected to two or more implantable discharge electrodes adapted to be located in a human patient to treat cardiac dysrhythmias, the method comprising the device implemented steps of:
   a) providing a charge storage system having a characteristic time constant of less than about 3 milliseconds;
   b) providing a discharge system electrically connected to the two or more implanted discharge electrodes;
   c) providing a control system electrically connected between the charge storage system and the discharge system;
   d) sensing a cardiac dysrhythmia in the human heart;
   e) charging the charge storage system to a voltage in response to the cardiac dysrhythmia;
   f) discharging the charge storage system in response to sensing a cardiac dysrhythmia; and
   g) controlling the discharge current by selectively interrupting the discharge from the charge storage system to effectively lengthen a discharge time of the discharge current to a time period appropriate for treatment of the cardiac dysrhythmia sensed.

7. The method of claim 6 wherein the charge storage system has a charge storage capacitance value that is less than about 60 μF.

8. An improved implantable cardioverter defibrillator apparatus electrically connected to two or more implantable discharge electrodes adapted to be located in a human patient for treating cardiac dysrhythmias, the apparatus having a sensing means for sensing a cardiac dysrhythmia, charge storage means for storing an electrical charge, power source means for charging the charge storage means, discharge means for selectively discharging the charge storage means into the two or more implanted discharge electrodes to deliver the electrical charge as a cardioversion countershock, the improvement comprising:
   a) charge storage means for storing an electric charge to be delivered to the two or more implanted electrodes, the charge storage means having a charge storage means capacitance value that is less than about 60 μF and the charge storage means and the implanted electrode having a time constant defined by an inter-electrode resistance value multiplied by a charge storage means capacitance value that is substantially at or below a maximum defibrillation chronaxie duration for the human patient heart of about 5 milliseconds: and b) control means electrically connected between the charge storage means and the discharge means for periodically interrupting the output of the charge storage means to the discharge means to effectively lengthen the discharge time of the cardioversion countershock to a period appropriate for the treatment desired for the cardiac dysrhythmia sensed.

* * * * *